(12) United States Patent
Ferrera

(10) Patent No.: US 8,545,514 B2
(45) Date of Patent: Oct. 1, 2013

(54) MONORAIL NEURO-MICROCATHETER FOR DELIVERY OF MEDICAL DEVICES TO TREAT STROKE, PROCESSES AND PRODUCTS THEREBY

(75) Inventor: David A. Ferrera, Redondo Beach, CA (US)

(73) Assignee: Covidien LP, Mansfield, MA (US)

( * ) Notice: Subject to any disclaimer, the term of this patent is extended or adjusted under 35 U.S.C. 154(b) by 356 days.

(21) Appl. No.: 12/422,105

(22) Filed: Apr. 10, 2009

(65) Prior Publication Data

US 2010/0100106 A1  Apr. 22, 2010

Related U.S. Application Data

(60) Provisional application No. 61/044,392, filed on Apr. 11, 2008, provisional application No. 61/057,613, filed on May 30, 2008, provisional application No. 61/166,725, filed on Apr. 4, 2009.

(51) Int. Cl.
*A61B 17/221* (2006.01)

(52) U.S. Cl.
USPC .......................................................... 606/127

(58) Field of Classification Search
USPC ................ 606/127, 128, 159, 200; 623/1.11, 623/1.12, 1.23
See application file for complete search history.

(56) References Cited

U.S. PATENT DOCUMENTS

| | | | |
|---|---|---|---|
| 2,709,999 A | 6/1955 | Nagel | |
| 3,174,851 A | 3/1965 | Buehler et al. | |
| 3,351,463 A | 11/1967 | Rozner et al. | |
| 3,506,171 A | 4/1970 | Rupert | |
| 3,753,700 A | 8/1973 | Harrison et al. | |
| 4,650,466 A | 3/1987 | Luther | |
| 4,993,481 A | 2/1991 | Kamimoto et al. | |
| 4,998,539 A | 3/1991 | Delsanti | |
| 5,035,686 A | 7/1991 | Crittenden et al. | |
| 5,057,114 A | 10/1991 | Wittich et al. | |
| 5,222,964 A | 6/1993 | Cooper | |
| 5,222,971 A | 6/1993 | Willard et al. | |
| 5,275,622 A | 1/1994 | Lazarus et al. | |
| 5,327,885 A | 7/1994 | Griffith | |
| 5,344,395 A | 9/1994 | Whalen | |
| 5,370,653 A | 12/1994 | Cragg | |
| 5,425,739 A | 6/1995 | Jessen | |
| 5,449,372 A | 9/1995 | Schmaltz | |
| 5,456,667 A | 10/1995 | Ham et al. | |

(Continued)

FOREIGN PATENT DOCUMENTS

| | | |
|---|---|---|
| EP | 0321912 | 6/1989 |
| EP | 1000590 | 5/2000 |

(Continued)

OTHER PUBLICATIONS

US 5,485,450, 8/1998, Mische et al. (withdrawn).

(Continued)

*Primary Examiner* — Ryan Severson
(74) *Attorney, Agent, or Firm* — Mark J. Kertz, Esq.

(57) ABSTRACT

Devices, processes and systems facilitate and enable treatment of acute stroke conditions, providing reperfusion while therapy is made available by preserving structure in the arterial tree. Using a Rapid Exchange approach with at least dual lumens in a microcatheter facilitates embolus/clot removal without damaging sensitive vasculature.

10 Claims, 4 Drawing Sheets

(56) References Cited

U.S. PATENT DOCUMENTS

| | | |
|---|---|---|
| 5,527,282 A | 6/1996 | Segal |
| 5,643,309 A | 7/1997 | Myler et al. |
| 5,649,906 A | 7/1997 | Gory et al. |
| 5,653,743 A | 8/1997 | Martin |
| 5,681,336 A | 10/1997 | Clement et al. |
| 5,683,449 A | 11/1997 | Marcade |
| 5,695,469 A | 12/1997 | Segal |
| 5,718,724 A | 2/1998 | Goicoechea et al. |
| 5,792,157 A | 8/1998 | Mische et al. |
| 5,795,322 A | 8/1998 | Boudewijn |
| 5,800,457 A | 9/1998 | Gelbfish |
| 5,800,519 A | 9/1998 | Sandock |
| 5,827,324 A | 10/1998 | Cassell et al. |
| 5,853,419 A | 12/1998 | Imran |
| 5,916,235 A | 6/1999 | Guglielmi |
| 5,922,019 A | 7/1999 | Hankh et al. |
| 5,928,260 A | 7/1999 | Chin |
| 5,938,671 A | 8/1999 | Katoh |
| 5,938,697 A | 8/1999 | Killion et al. |
| 5,941,895 A | 8/1999 | Myler et al. |
| 5,947,995 A | 9/1999 | Samuels |
| 5,951,599 A | 9/1999 | McCrory |
| 5,961,547 A | 10/1999 | Razavi |
| 5,968,013 A | 10/1999 | Smith et al. |
| 5,972,016 A | 10/1999 | Morales |
| 5,972,019 A | 10/1999 | Engelson |
| 5,972,219 A | 10/1999 | Habets |
| 5,976,120 A | 11/1999 | Chow et al. |
| 5,980,514 A | 11/1999 | Kupiecki et al. |
| 6,001,118 A | 12/1999 | Daniel et al. |
| 6,010,449 A | 1/2000 | Selmon et al. |
| 6,010,498 A | 1/2000 | Guglielmi |
| 6,010,521 A | 1/2000 | Lee et al. |
| 6,015,424 A | 1/2000 | Rosenbluth et al. |
| 6,039,721 A | 3/2000 | Johnson |
| 6,051,020 A | 4/2000 | Goicoechea et al. |
| 6,063,070 A | 5/2000 | Eder |
| 6,063,104 A | 5/2000 | Villar et al. |
| 6,063,111 A | 5/2000 | Hieshima et al. |
| 6,066,149 A | 5/2000 | Samson et al. |
| 6,066,158 A | 5/2000 | Engelson |
| 6,093,199 A | 7/2000 | Brown et al. |
| 6,096,034 A | 8/2000 | Kupiecki et al. |
| 6,106,548 A | 8/2000 | Roubin et al. |
| 6,117,167 A | 9/2000 | Goicoechea et al. |
| 6,123,115 A | 9/2000 | Greenhalgh |
| 6,136,006 A | 10/2000 | Johnson et al. |
| 6,146,396 A | 11/2000 | Konya et al. |
| 6,159,238 A | 12/2000 | Killion et al. |
| 6,159,239 A | 12/2000 | Greenhalgh |
| 6,164,339 A | 12/2000 | Greenhalgh |
| 6,168,592 B1 | 1/2001 | Kupiecki et al. |
| 6,168,604 B1 | 1/2001 | Cano |
| 6,190,358 B1 | 2/2001 | Fitzmaurice |
| 6,192,944 B1 | 2/2001 | Greenhalgh |
| 6,193,708 B1 | 2/2001 | Ken et al. |
| 6,210,364 B1 | 4/2001 | Anderson |
| 6,217,609 B1 | 4/2001 | Haverkost |
| 6,221,096 B1 | 4/2001 | Aiba et al. |
| 6,231,598 B1 | 5/2001 | Berry et al. |
| 6,238,430 B1 | 5/2001 | Klumb et al. |
| 6,280,413 B1 | 8/2001 | Clark et al. |
| 6,283,940 B1 | 9/2001 | Mullholland |
| 6,283,992 B1 | 9/2001 | Hankh et al. |
| 6,290,720 B1 | 9/2001 | Khosravi et al. |
| 6,302,906 B1 | 10/2001 | Goicoechea et al. |
| 6,305,436 B1 | 10/2001 | Andersen et al. |
| 6,306,141 B1 | 10/2001 | Jervis |
| 6,322,585 B1 | 11/2001 | Khosravi et al. |
| 6,325,815 B1 | 12/2001 | Kusleika et al. |
| 6,325,820 B1 | 12/2001 | Khosravi et al. |
| 6,325,822 B1 | 12/2001 | Chouinard et al. |
| 6,344,041 B1 | 2/2002 | Kupiecki et al. |
| 6,383,205 B1 | 5/2002 | Samson et al. |
| 6,390,993 B1 | 5/2002 | Cornish et al. |
| 6,402,771 B1 | 6/2002 | Palmer et al. |
| 6,454,780 B1 | 9/2002 | Wallace |
| 6,458,139 B1 | 10/2002 | Palmer et al. |
| 6,468,301 B1 | 10/2002 | Amplatz et al. |
| 6,475,236 B1 | 11/2002 | Roubin et al. |
| 6,475,237 B2 | 11/2002 | Drasler et al. |
| 6,485,500 B1 | 11/2002 | Kokish |
| 6,485,509 B2 | 11/2002 | Killion et al. |
| 6,537,294 B1 * | 3/2003 | Boyle et al. .................. 606/200 |
| 6,551,341 B2 | 4/2003 | Boylan et al. |
| 6,551,342 B1 | 4/2003 | Shen et al. |
| 6,553,810 B2 | 4/2003 | Webb et al. |
| 6,554,856 B1 | 4/2003 | Doorly et al. |
| 6,558,405 B1 | 5/2003 | McInnes |
| 6,562,066 B1 | 5/2003 | Martin |
| 6,569,179 B2 | 5/2003 | Teoh et al. |
| 6,569,193 B1 | 5/2003 | Cox et al. |
| 6,575,997 B1 | 6/2003 | Palmer et al. |
| 6,589,265 B1 | 7/2003 | Palmer et al. |
| 6,592,607 B1 * | 7/2003 | Palmer et al. ................. 606/200 |
| 6,592,615 B1 | 7/2003 | Marcade et al. |
| 6,605,057 B2 | 8/2003 | Fitzmaurice |
| 6,610,077 B1 | 8/2003 | Hancock et al. |
| 6,616,617 B1 | 9/2003 | Ferrera et al. |
| 6,629,953 B1 | 10/2003 | Boyd |
| 6,632,241 B1 | 10/2003 | Hancock et al. |
| 6,635,081 B2 | 10/2003 | Khosravi et al. |
| 6,638,294 B1 | 10/2003 | Palmer |
| 6,641,590 B1 | 11/2003 | Palmer et al. |
| 6,652,505 B1 | 11/2003 | Tsugita |
| 6,652,576 B1 | 11/2003 | Stalker |
| 6,660,021 B1 | 12/2003 | Palmer et al. |
| 6,663,607 B2 | 12/2003 | Slaikeu et al. |
| 6,666,829 B2 | 12/2003 | Cornish et al. |
| 6,669,723 B2 | 12/2003 | Killion et al. |
| 6,673,025 B1 | 1/2004 | Richardson et al. |
| 6,685,722 B1 | 2/2004 | Rosenbluth |
| 6,685,738 B2 | 2/2004 | Chouinard et al. |
| 6,695,813 B1 | 2/2004 | Boyle et al. |
| 6,702,843 B1 | 3/2004 | Brown et al. |
| 6,709,440 B2 | 3/2004 | Callol et al. |
| 6,716,178 B1 | 4/2004 | Kilpatrick et al. |
| 6,723,112 B2 | 4/2004 | Ho et al. |
| 6,730,104 B1 | 5/2004 | Sepetka et al. |
| 6,733,519 B2 | 5/2004 | Lashinski |
| 6,746,468 B1 | 6/2004 | Sepetka et al. |
| 6,764,506 B2 | 7/2004 | Roubin et al. |
| 6,773,454 B2 | 8/2004 | Wholey et al. |
| 6,790,237 B2 | 9/2004 | Stinson |
| 6,795,979 B2 | 9/2004 | Fournier |
| 6,802,851 B2 | 10/2004 | Jones et al. |
| 6,818,015 B2 | 11/2004 | Hankh et al. |
| 6,821,291 B2 | 11/2004 | Bolea et al. |
| 6,824,558 B2 | 11/2004 | Parodi |
| 6,833,003 B2 | 12/2004 | Jones et al. |
| 6,840,958 B2 | 1/2005 | Nunez et al. |
| 6,881,220 B2 | 4/2005 | Edwin et al. |
| 6,893,413 B2 | 5/2005 | Martin |
| 6,913,612 B2 | 7/2005 | Palmer et al. |
| 6,949,620 B2 | 9/2005 | Aida et al. |
| 6,953,472 B2 | 10/2005 | Palmer et al. |
| 6,955,685 B2 | 10/2005 | Escamilla et al. |
| 6,960,227 B2 | 11/2005 | Jones et al. |
| 6,991,641 B2 | 1/2006 | Diaz et al. |
| 6,994,723 B1 | 2/2006 | McMahon |
| 7,001,422 B2 | 2/2006 | Escamilla et al. |
| 7,004,954 B1 | 2/2006 | Voss |
| 7,004,955 B2 | 2/2006 | Shen et al. |
| 7,004,956 B2 | 2/2006 | Palmer et al. |
| 7,018,401 B1 | 3/2006 | Hyodoh et al. |
| 7,029,688 B2 | 4/2006 | Hubbell et al. |
| 7,037,329 B2 | 5/2006 | Martin |
| 7,041,116 B2 | 5/2006 | Goto et al. |
| 7,048,014 B2 | 5/2006 | Hyodoh et al. |
| 7,056,328 B2 | 6/2006 | Arnott |
| 7,056,336 B2 | 6/2006 | Armstrong et al. |
| 7,060,091 B2 | 6/2006 | Killion et al. |
| 7,089,218 B1 | 8/2006 | Visel |
| 7,112,217 B1 | 9/2006 | Kugler et al. |

| | | |
|---|---|---|
| 7,118,600 B2 | 10/2006 | Dua et al. |
| 7,125,419 B2 | 10/2006 | Sequin et al. |
| 7,128,736 B1 | 10/2006 | Abrams et al. |
| 7,144,421 B2 | 12/2006 | Carpenter et al. |
| 7,147,655 B2 | 12/2006 | Chermoni |
| 7,147,660 B2 | 12/2006 | Chobotov et al. |
| 7,156,869 B1 | 1/2007 | Pacetti |
| 7,160,317 B2 | 1/2007 | McHale |
| 7,169,165 B2 | 1/2007 | Belef et al. |
| 7,172,575 B2 | 2/2007 | El-Nounou |
| 7,172,617 B2 | 2/2007 | Colgan et al. |
| 7,175,607 B2 | 2/2007 | Lim |
| 7,179,273 B1 | 2/2007 | Palmer et al. |
| 7,179,284 B2 | 2/2007 | Khosravi et al. |
| 7,201,769 B2 | 4/2007 | Jones et al. |
| 7,201,770 B2 | 4/2007 | Johnson |
| 7,223,284 B2 | 5/2007 | Khosravi et al. |
| 7,238,197 B2 | 7/2007 | Sequin et al. |
| 7,240,516 B2 | 7/2007 | Pryor |
| 7,241,301 B2 | 7/2007 | Thramann et al. |
| 7,279,003 B2 | 10/2007 | Berra et al. |
| 7,279,292 B2 | 10/2007 | Imam et al. |
| 7,285,126 B2 | 10/2007 | Sepetka et al. |
| 7,294,147 B2 | 11/2007 | Hartley |
| 7,300,458 B2 | 11/2007 | Henkes et al. |
| 7,306,619 B1 | 12/2007 | Palmer |
| 7,309,345 B2 | 12/2007 | Wallace |
| 7,309,351 B2 | 12/2007 | Escamilla |
| 7,323,000 B2 | 1/2008 | Monstdt et al. |
| 7,323,005 B2 | 1/2008 | Wallace et al. |
| 7,323,006 B2 | 1/2008 | Andreas et al. |
| 7,326,240 B1 | 2/2008 | Caro et al. |
| 7,344,550 B2 | 3/2008 | Carrison et al. |
| 7,344,556 B2 | 3/2008 | Sequin et al. |
| 7,351,255 B2 | 4/2008 | Andreas |
| 7,354,455 B2 | 4/2008 | Stinson |
| 7,402,169 B2 | 7/2008 | Killion et al. |
| 7,407,509 B2 | 8/2008 | Greenberg et al. |
| 7,435,254 B2 | 10/2008 | Chouinard et al. |
| 7,438,720 B2 | 10/2008 | Shaked |
| 7,455,646 B2 | 11/2008 | Richardson et al. |
| 7,473,272 B2 | 1/2009 | Pryor |
| 7,494,474 B2 | 2/2009 | Richardson et al. |
| 7,549,974 B2 | 6/2009 | Nayak |
| 7,691,122 B2 | 4/2010 | Dieck et al. |
| 7,727,242 B2 | 6/2010 | Sepetka et al. |
| 7,727,243 B2 | 6/2010 | Sepetka et al. |
| 7,749,243 B2 | 7/2010 | Phung |
| 7,780,694 B2 | 8/2010 | Palmer et al. |
| 7,833,240 B2 | 11/2010 | Okushi et al. |
| 7,972,342 B2 | 7/2011 | Gandhi et al. |
| 8,052,640 B2 | 11/2011 | Fiorella et al. |
| 8,062,307 B2 | 11/2011 | Sepetka et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,918 B2 | 1/2012 | Gandhi et al. |
| 8,100,935 B2 | 1/2012 | Rosenbluth et al. |
| 8,105,333 B2 | 1/2012 | Sepetka et al. |
| 8,197,493 B2 | 6/2012 | Ferrera et al. |
| 2001/0000797 A1 | 5/2001 | Mazzocchi |
| 2001/0004705 A1 | 6/2001 | Killion et al. |
| 2001/0010013 A1 | 7/2001 | Cox et al. |
| 2001/0031981 A1 | 10/2001 | Evans et al. |
| 2001/0034531 A1 | 10/2001 | Ho et al. |
| 2001/0044633 A1 | 11/2001 | Klint |
| 2001/0044647 A1 | 11/2001 | Pinchuk et al. |
| 2001/0047202 A1 | 11/2001 | Slaikeu et al. |
| 2001/0051823 A1 | 12/2001 | Khosravi et al. |
| 2002/0004681 A1 | 1/2002 | Teoh et al. |
| 2002/0007210 A1 | 1/2002 | Chouinard et al. |
| 2002/0016564 A1 | 2/2002 | Courtney et al. |
| 2002/0016624 A1 | 2/2002 | Patterson |
| 2002/0032479 A1 | 3/2002 | Hankh et al. |
| 2002/0038142 A1 | 3/2002 | Khosravi et al. |
| 2002/0038146 A1 | 3/2002 | Harry |
| 2002/0052643 A1 | 5/2002 | Wholey et al. |
| 2002/0068968 A1 | 6/2002 | Hupp |
| 2002/0072790 A1 | 6/2002 | McGuckin, Jr. et al. |
| 2002/0087209 A1 | 7/2002 | Edwin et al. |
| 2002/0091355 A1 | 7/2002 | Hayden |
| 2002/0095141 A1 | 7/2002 | Belef |
| 2002/0143387 A1 | 10/2002 | Soetikno et al. |
| 2002/0161377 A1 | 10/2002 | Rabkin |
| 2002/0169458 A1 | 11/2002 | Connors |
| 2002/0183831 A1 | 12/2002 | Rolando et al. |
| 2002/0198588 A1 | 12/2002 | Armstrong et al. |
| 2003/0004536 A1 | 1/2003 | Boylan et al. |
| 2003/0023230 A1 | 1/2003 | Lewis et al. |
| 2003/0023299 A1 | 1/2003 | Amplatz et al. |
| 2003/0032941 A1 | 2/2003 | Boyle et al. |
| 2003/0032977 A1 | 2/2003 | Brady |
| 2003/0040771 A1 | 2/2003 | Hyodoh et al. |
| 2003/0040772 A1 | 2/2003 | Hyodoh et al. |
| 2003/0055440 A1 | 3/2003 | Jones et al. |
| 2003/0055451 A1 | 3/2003 | Jones et al. |
| 2003/0074056 A1 | 4/2003 | Killion et al. |
| 2003/0078605 A1 | 4/2003 | Bashiri et al. |
| 2003/0097114 A1 | 5/2003 | Ouriel et al. |
| 2003/0105484 A1 | 6/2003 | Boyle |
| 2003/0125791 A1 | 7/2003 | Sequin et al. |
| 2003/0125798 A1 | 7/2003 | Martin |
| 2003/0130719 A1 | 7/2003 | Martin |
| 2003/0139796 A1 | 7/2003 | Sequin et al. |
| 2003/0139803 A1 | 7/2003 | Sequin et al. |
| 2003/0149475 A1 | 8/2003 | Hyodoh et al. |
| 2003/0153944 A1 | 8/2003 | Phung et al. |
| 2003/0176914 A1 | 9/2003 | Rabkin et al. |
| 2003/0199921 A1 | 10/2003 | Palmer et al. |
| 2003/0204202 A1 | 10/2003 | Palmer et al. |
| 2004/0002752 A1 | 1/2004 | Griffin et al. |
| 2004/0006306 A1 | 1/2004 | Evans et al. |
| 2004/0006381 A1 | 1/2004 | Sequin et al. |
| 2004/0019322 A1 | 1/2004 | Hoffmann |
| 2004/0030378 A1 | 2/2004 | Khosravi et al. |
| 2004/0034386 A1 | 2/2004 | Fulton et al. |
| 2004/0049258 A1 | 3/2004 | Khosravi et al. |
| 2004/0054367 A1 | 3/2004 | Jimenez, Jr. et al. |
| 2004/0059259 A1 | 3/2004 | Cornish et al. |
| 2004/0059407 A1 | 3/2004 | Escamilla et al. |
| 2004/0068288 A1 | 4/2004 | Palmer et al. |
| 2004/0073300 A1 | 4/2004 | Chouinard et al. |
| 2004/0078071 A1 | 4/2004 | Escamilla et al. |
| 2004/0079429 A1 | 4/2004 | Miller et al. |
| 2004/0088002 A1 | 5/2004 | Boyle et al. |
| 2004/0102838 A1 | 5/2004 | Killion et al. |
| 2004/0106979 A1 | 6/2004 | Goicoechea et al. |
| 2004/0114912 A1 | 6/2004 | Okamoto et al. |
| 2004/0117003 A1 | 6/2004 | Ouriel et al. |
| 2004/0147939 A1 | 7/2004 | Rabkin et al. |
| 2004/0158307 A1 | 8/2004 | Jones et al. |
| 2004/0158312 A1 | 8/2004 | Chouinard et al. |
| 2004/0186562 A1 | 9/2004 | Cox |
| 2004/0193246 A1 | 9/2004 | Ferrera |
| 2004/0199201 A1 | 10/2004 | Kellett et al. |
| 2004/0215312 A1 | 10/2004 | Andreas |
| 2004/0215319 A1 | 10/2004 | Berra et al. |
| 2004/0249439 A1 | 12/2004 | Richter et al. |
| 2004/0254628 A1 | 12/2004 | Nazzaro et al. |
| 2004/0260385 A1 | 12/2004 | Jones et al. |
| 2005/0033334 A1 | 2/2005 | Santra et al. |
| 2005/0033349 A1 | 2/2005 | Jones et al. |
| 2005/0033409 A1 | 2/2005 | Burke et al. |
| 2005/0038447 A1 | 2/2005 | Huffmaster |
| 2005/0038468 A1 | 2/2005 | Panetta et al. |
| 2005/0038496 A1 | 2/2005 | Jones et al. |
| 2005/0049676 A1 | 3/2005 | Nazzaro et al. |
| 2005/0060017 A1 | 3/2005 | Fischell et al. |
| 2005/0075715 A1 | 4/2005 | Borges et al. |
| 2005/0080480 A1 | 4/2005 | Bolea et al. |
| 2005/0090857 A1 | 4/2005 | Kusleika et al. |
| 2005/0096726 A1 | 5/2005 | Sequin et al. |
| 2005/0102018 A1 | 5/2005 | Carpenter et al. |
| 2005/0107823 A1 | 5/2005 | Leone et al. |
| 2005/0119684 A1 | 6/2005 | Guterman |
| 2005/0125023 A1 | 6/2005 | Bates |
| 2005/0126979 A1 | 6/2005 | Lowe |
| 2005/0131515 A1 | 6/2005 | Cully et al. |

| | | | | | |
|---|---|---|---|---|---|
| 2005/0131516 A1 | 6/2005 | Greenhalgh | 2007/0288037 A1 | 12/2007 | Cheng et al. |
| 2005/0159774 A1 | 7/2005 | Belef | 2007/0288080 A1 | 12/2007 | Maccollum et al. |
| 2005/0177228 A1 | 8/2005 | Solem et al. | 2007/0288083 A1 | 12/2007 | Hines |
| 2005/0187612 A1 | 8/2005 | Edwin | 2007/0293846 A1 | 12/2007 | von Oepen et al. |
| 2005/0192661 A1 | 9/2005 | Griffen et al. | 2007/0299503 A1 | 12/2007 | Berra et al. |
| 2005/0209673 A1 | 9/2005 | Shaked | 2008/0001333 A1 | 1/2008 | Kleine et al. |
| 2005/0209675 A1 | 9/2005 | Ton et al. | 2008/0015558 A1 | 1/2008 | Harlan |
| 2005/0209678 A1 | 9/2005 | Henkes et al. | 2008/0015682 A1 | 1/2008 | Majercak et al. |
| 2005/0216050 A1 | 9/2005 | Sepetka et al. | 2008/0033528 A1 | 2/2008 | Satasiya et al. |
| 2005/0222583 A1 | 10/2005 | Cano | 2008/0039926 A1 | 2/2008 | Majercak et al. |
| 2005/0222607 A1 | 10/2005 | Palmer et al. | 2008/0039930 A1 | 2/2008 | Jones et al. |
| 2005/0267570 A1 | 12/2005 | Shadduck | 2008/0045995 A1 | 2/2008 | Guterman et al. |
| 2005/0277978 A1 | 12/2005 | Greenhalgh | 2008/0046064 A1 | 2/2008 | Sequin et al. |
| 2006/0020285 A1 | 1/2006 | Niermann | 2008/0046072 A1 | 2/2008 | Laborde et al. |
| 2006/0020321 A1 | 1/2006 | Parker | 2008/0051803 A1 | 2/2008 | Monjtadt |
| 2006/0025845 A1 | 2/2006 | Escamilla et al. | 2008/0058724 A1 | 3/2008 | Wallace et al. |
| 2006/0025850 A1 | 2/2006 | Feller et al. | 2008/0071178 A1 | 3/2008 | Greenland et al. |
| 2006/0030865 A1 | 2/2006 | Balg | 2008/0077175 A1 | 3/2008 | Palmer |
| 2006/0036281 A1 | 2/2006 | Patterson | 2008/0082159 A1 | 4/2008 | Tseng et al. |
| 2006/0052816 A1 | 3/2006 | Bates et al. | 2008/0086196 A1 | 4/2008 | Truckai et al. |
| 2006/0058833 A1 | 3/2006 | VanCamp | 2008/0097495 A1 | 4/2008 | Feller et al. |
| 2006/0058836 A1 | 3/2006 | Bose et al. | 2008/0103477 A1 | 5/2008 | Jones |
| 2006/0058838 A1 | 3/2006 | Bose et al. | 2008/0103585 A1 | 5/2008 | Monstadt |
| 2006/0074480 A1 | 4/2006 | Bales et al. | 2008/0109063 A1 | 5/2008 | Hancock et al. |
| 2006/0089703 A1 | 4/2006 | Escamilla et al. | 2008/0109067 A1 | 5/2008 | Caro et al. |
| 2006/0100663 A1 | 5/2006 | Palmer et al. | 2008/0114445 A1 | 5/2008 | Melsheimer et al. |
| 2006/0106421 A1 | 5/2006 | Teoh | 2008/0125855 A1 | 5/2008 | Henkes et al. |
| 2006/0106448 A1 | 5/2006 | Shaked | 2008/0140107 A1 | 6/2008 | Bei et al. |
| 2006/0122685 A1 | 6/2006 | Bonsignore et al. | 2008/0140181 A1 | 6/2008 | Reynolds et al. |
| 2006/0135947 A1 | 6/2006 | Soltesz et al. | 2008/0147100 A1 | 6/2008 | Wallace et al. |
| 2006/0142841 A1 | 6/2006 | Khosravi et al. | 2008/0161903 A1 | 7/2008 | Sequin et al. |
| 2006/0142849 A1 | 6/2006 | Killion et al. | 2008/0161936 A1 | 7/2008 | Feller et al. |
| 2006/0195172 A1 | 8/2006 | Luo et al. | 2008/0167708 A1 | 7/2008 | Molland et al. |
| 2006/0200048 A1 | 9/2006 | Furst et al. | 2008/0195140 A1 | 8/2008 | Myla et al. |
| 2006/0200221 A1 | 9/2006 | Malewicz | 2008/0200946 A1 | 8/2008 | Braun et al. |
| 2006/0224180 A1 | 10/2006 | Anderson et al. | 2008/0208319 A1 | 8/2008 | Rabkin et al. |
| 2006/0229645 A1 | 10/2006 | Bonnette et al. | 2008/0221554 A1 | 9/2008 | O'Connor et al. |
| 2006/0259119 A1 | 11/2006 | Rucker | 2008/0221600 A1 | 9/2008 | Dieck et al. |
| 2006/0265054 A1 | 11/2006 | Greenhalgh et al. | 2008/0221664 A1 | 9/2008 | Bales et al. |
| 2006/0271090 A1 | 11/2006 | Shaked et al. | 2008/0221671 A1 | 9/2008 | Chouinard et al. |
| 2006/0276883 A1 | 12/2006 | Greenberg et al. | 2008/0228216 A1 | 9/2008 | Strauss et al. |
| 2006/0287701 A1 | 12/2006 | Pal | 2008/0234795 A1 | 9/2008 | Snow et al. |
| 2006/0287704 A1 | 12/2006 | Hartley et al. | 2008/0243229 A1 | 10/2008 | Wallace et al. |
| 2007/0032852 A1 | 2/2007 | Machek et al. | 2008/0243232 A1 | 10/2008 | Hegg et al. |
| 2007/0043424 A1 | 2/2007 | Pryor | 2008/0247943 A1 | 10/2008 | Lanza et al. |
| 2007/0043425 A1 | 2/2007 | Hartley et al. | 2008/0249598 A1 | 10/2008 | Sherry |
| 2007/0055299 A1 | 3/2007 | Ishimaru et al. | 2008/0255678 A1 | 10/2008 | Cully et al. |
| 2007/0055358 A1 | 3/2007 | Krolik et al. | 2008/0262506 A1 | 10/2008 | Griffin et al. |
| 2007/0055360 A1 | 3/2007 | Hanson et al. | 2008/0262528 A1 | 10/2008 | Martin |
| 2007/0055365 A1 | 3/2007 | Greenberg et al. | 2008/0262532 A1 | 10/2008 | Martin |
| 2007/0067011 A1 | 3/2007 | Krolik et al. | 2008/0262592 A1 | 10/2008 | Jordan et al. |
| 2007/0073376 A1 | 3/2007 | Krolik et al. | 2008/0262952 A1 | 10/2008 | Channell |
| 2007/0088387 A1 | 4/2007 | Eskridge et al. | 2008/0269774 A1 | 10/2008 | Garcia et al. |
| 2007/0100425 A1 | 5/2007 | Sequin et al. | 2008/0269868 A1 | 10/2008 | Bei et al. |
| 2007/0118205 A1 | 5/2007 | Davidson et al. | 2008/0275497 A1 | 11/2008 | Palmer et al. |
| 2007/0123972 A1 | 5/2007 | Greenberg et al. | 2008/0275498 A1 | 11/2008 | Palmer et al. |
| 2007/0135888 A1 | 6/2007 | Khosravi et al. | 2008/0275536 A1 | 11/2008 | Zarins et al. |
| 2007/0141036 A1 | 6/2007 | Gorrochategui Barrueta et al. | 2008/0281302 A1 | 11/2008 | Murphy et al. |
| 2007/0142896 A1 | 6/2007 | Anderson et al. | 2008/0281350 A1 | 11/2008 | Sepetka et al. |
| 2007/0156170 A1 | 7/2007 | Hancock et al. | 2008/0281393 A1 | 11/2008 | Armstrong et al. |
| 2007/0156228 A1 | 7/2007 | Majercak et al. | 2008/0281397 A1 | 11/2008 | Killion et al. |
| 2007/0162109 A1 | 7/2007 | Davila et al. | 2008/0281403 A1 | 11/2008 | Kavteladze |
| 2007/0191866 A1 | 8/2007 | Palmer et al. | 2008/0306503 A1 | 12/2008 | Que et al. |
| 2007/0191884 A1 | 8/2007 | Eskridge et al. | 2008/0306504 A1 | 12/2008 | Win et al. |
| 2007/0191924 A1 | 8/2007 | Rudakov | 2008/0312732 A1 | 12/2008 | Hartley et al. |
| 2007/0198028 A1 | 8/2007 | Miloslavski | 2008/0319525 A1 | 12/2008 | Tieu et al. |
| 2007/0198030 A1 | 8/2007 | Martin et al. | 2008/0319533 A1 | 12/2008 | Lehe |
| 2007/0198075 A1 | 8/2007 | Levy | 2009/0018633 A1 | 1/2009 | Lindquist et al. |
| 2007/0203452 A1 | 8/2007 | Mehta | 2009/0018634 A1 | 1/2009 | State |
| 2007/0203559 A1 | 8/2007 | Freudenthal et al. | 2009/0018640 A1 | 1/2009 | State |
| 2007/0208367 A1 | 9/2007 | Fiorella | 2009/0024157 A1 | 1/2009 | Anukhin |
| 2007/0208371 A1 | 9/2007 | French et al. | 2009/0025820 A1 | 1/2009 | Adams |
| 2007/0219621 A1 | 9/2007 | Hartley et al. | 2009/0030502 A1 | 1/2009 | Sun et al. |
| 2007/0225794 A1 | 9/2007 | Thramann et al. | 2009/0036968 A1 | 2/2009 | Hepworth et al. |
| 2007/0233236 A1 | 10/2007 | Pryor | 2009/0036977 A1 | 2/2009 | Rassat et al. |
| 2007/0250040 A1 | 10/2007 | Provost et al. | 2009/0062726 A1 | 3/2009 | Ford et al. |
| 2007/0266542 A1 | 11/2007 | Melsheimer | 2009/0062773 A1 | 3/2009 | Cornish et al. |
| 2007/0270932 A1 | 11/2007 | Headley et al. | 2009/0062834 A1 | 3/2009 | Moftakhar et al. |
| 2007/0288034 A1 | 12/2007 | MacCollum et al. | 2009/0068097 A1 | 3/2009 | Sevrain |

| | | | |
|---|---|---|---|
| 2009/0069828 A1 | 3/2009 | Martin et al. |
| 2009/0069836 A1 | 3/2009 | Labdag et al. |
| 2009/0076450 A1 | 3/2009 | Caizza et al. |
| 2009/0082800 A1 | 3/2009 | Janardhan |
| 2009/0093822 A1 | 4/2009 | Ducharme |
| 2009/0105644 A1 | 4/2009 | Leonard et al. |
| 2009/0105722 A1 | 4/2009 | Fulkerson |
| 2009/0105737 A1 | 4/2009 | Fulkerson |
| 2009/0105747 A1 | 4/2009 | Chanduszko et al. |
| 2009/0125053 A1 | 5/2009 | Ferrera et al. |
| 2009/0192455 A1 | 7/2009 | Ferrera et al. |
| 2009/0292297 A1 | 11/2009 | Ferrera |
| 2009/0299393 A1 | 12/2009 | Martin et al. |
| 2010/0022951 A1 | 1/2010 | Ferrera et al. |
| 2010/0114017 A1 | 5/2010 | Lenker et al. |
| 2010/0114135 A1 | 5/2010 | Wilson et al. |
| 2010/0137892 A1 | 6/2010 | Krolik et al. |
| 2010/0152766 A1 | 6/2010 | Dieck et al. |
| 2010/0174309 A1 | 7/2010 | Fulkerson et al. |
| 2010/0217187 A1 | 8/2010 | Fulkerson et al. |
| 2010/0256600 A1 | 10/2010 | Ferrera |
| 2010/0318097 A1 | 12/2010 | Ferrera et al. |
| 2011/0009875 A1 | 1/2011 | Grandfield et al. |
| 2011/0009941 A1 | 1/2011 | Grandfield et al. |
| 2011/0060212 A1 | 3/2011 | Slee et al. |
| 2011/0152920 A1 | 6/2011 | Eckhouse et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0172699 A1 | 7/2011 | Miller et al. |
| 2011/0184456 A1 | 7/2011 | Grandfield et al. |
| 2011/0190797 A1 | 8/2011 | Fulkerson et al. |
| 2011/0202088 A1 | 8/2011 | Eckhouse et al. |
| 2011/0238106 A1 | 9/2011 | Ferrera et al. |
| 2011/0270178 A1 | 11/2011 | Fiorella et al. |
| 2011/0288572 A1 | 11/2011 | Martin |
| 2011/0301686 A1 | 12/2011 | Bowman et al. |
| 2011/0319917 A1 | 12/2011 | Ferrera et al. |
| 2012/0016396 A1 | 1/2012 | Dehnad |
| 2012/0016406 A1 | 1/2012 | Ferrera et al. |
| 2012/0022576 A1 | 1/2012 | Ferrera et al. |
| 2012/0022581 A1 | 1/2012 | Wilson et al. |
| 2012/0035648 A1 | 2/2012 | Wilson et al. |
| 2012/0041411 A1 | 2/2012 | Horton et al. |
| 2012/0041449 A1 | 2/2012 | Eckhouse et al. |
| 2012/0041459 A1 | 2/2012 | Fiorella et al. |
| 2012/0041460 A1 | 2/2012 | Ferrera et al. |
| 2012/0041464 A1 | 2/2012 | Monetti et al. |
| 2012/0041474 A1 | 2/2012 | Eckhouse et al. |
| 2012/0041475 A1 | 2/2012 | Ferrera et al. |
| 2012/0046686 A1 | 2/2012 | Wilson et al. |
| 2012/0065660 A1 | 3/2012 | Ferrera et al. |
| 2012/0071964 A1 | 3/2012 | Cattaneo et al. |
| 2012/0078140 A1 | 3/2012 | Nita |
| 2012/0078285 A1 | 3/2012 | Griffin |
| 2012/0089216 A1 | 4/2012 | Rapaport et al. |
| 2012/0116443 A1 | 5/2012 | Ferrera et al. |

FOREIGN PATENT DOCUMENTS

| | | |
|---|---|---|
| EP | 1437097 | 7/2004 |
| EP | 2257248 B1 | 10/2011 |
| EP | 2301450 B1 | 11/2011 |
| EP | 2417919 A2 | 2/2012 |
| JP | 2006-094876 | 4/2006 |
| WO | WO-94/03127 A1 | 2/1994 |
| WO | WO98/55173 | 12/1998 |
| WO | WO00/32265 | 6/2000 |
| WO | WO00/53120 | 9/2000 |
| WO | WO-01/08743 | 2/2001 |
| WO | WO01/36034 | 5/2001 |
| WO | WO01/45569 | 6/2001 |
| WO | WO03/011188 | 2/2003 |
| WO | WO03/017823 | 3/2003 |
| WO | WO 2007/089897 | 8/2007 |
| WO | WO2007/121005 | 10/2007 |
| WO | WO 2008/117256 A2 | 10/2008 |
| WO | WO 2008/117257 A2 | 10/2008 |
| WO | WO-2008/124728 | 10/2008 |
| WO | WO2009/105710 | 8/2009 |
| WO | WO2009/124288 | 10/2009 |
| WO | WO2009/126747 | 10/2009 |
| WO | WO2010/010545 | 1/2010 |
| WO | WO2010/023671 | 3/2010 |
| WO | WO2010/046897 | 4/2010 |
| WO | WO2010/049121 | 5/2010 |
| WO | WO2010/062363 | 6/2010 |
| WO | WO2010/102307 | 9/2010 |
| WO | WO2010/115642 | 10/2010 |
| WO | WO-2010/121037 | 10/2010 |
| WO | WO-2010/121049 A9 | 12/2010 |
| WO | WO-2011/054531 A3 | 7/2011 |
| WO | WO-2011/095352 | 8/2011 |
| WO | WO-2011/133486 | 10/2011 |
| WO | WO-2011/135556 | 11/2011 |
| WO | WO-2011/144336 | 11/2011 |
| WO | WO-2011/147567 | 12/2011 |
| WO | WO-2012/009675 A2 | 1/2012 |
| WO | WO-2012/025245 | 3/2012 |
| WO | WO-2012/025247 | 3/2012 |

OTHER PUBLICATIONS

T.W. Duerig, D.E. Tolomeo, M. Wholey, An Overview of Superelastic Stent Design.

Michael E. Kelly, MD, et al., Recanalization of an Acute Middle Cerebral Artery Occlusion Using a Self-Expanding, Reconstrainable, Intracranial Microstent as a Temporary Endovascular Bypass; Stroke, Jun. 2008, pp. 1770-1773, vol. 39, issue 6, United States.

Eric Sauvegeau, MD et al., Middle Cerebral Artery Stenting for Acute Ischemic Stroke After Unsuccessful Merci Retrieval; Neurosurgery (Special Technical Report), Apr. 2007, pp. 701-706, vol. 60, issue 4, United States.

David M. Pelz, et al., Advances in Interventional Neuroradiology 2007; Stroke, Jan. 2008, pp. 268-272, vol. 39, issue 1, United States.

Philippa C. Lavallee, et al., Stent-Assisted Endovascular Thrombolysis Versus Intravenous Thrombolysis in Internal Carotid Artery Dissection with Tandem Internal Carotid and Middle Cerebral Artery Occlusion; Stroke, Aug. 2007, pp. 2270-2274, vol. 38, issue 8, United States.

E.I. Levy et al., Self-Expanding Stents for Recanalization of Acute Cerebrovascular Occlusions; AJNR, May 2007, pp. 816-822, vol. 28, United States.

Micro Therapeutics, Inc., DBA EV3 Neurovascular, Inc., Solitaire FR Revascularization Device, Instructions for Use, 70494-001 Rev. Mar. 2009.

Micro Therapeutics, Inc., DBA EV3 Neurovascular, Inc., Fully depoyable. Completely retrievable. Solitaire AB, Neurovascular Remodeling Device.

Robertson, Kathy, Stroke device startup lands National Science Foundation grant, Sacramento Business Journal, Oct. 23, 2009, Sacramento, California, USA.

Henkes, H. et al., "A Microcatheter-Delivered Highly-Flexible and Fully-Retrievable Stent, Specifically Designed for Intracranial Use," *Interventional Neuroradiology*, vol. 9, pp. 391-393 (Dec. 2003).

Doerfler, A. et al., "A Novel Flexible, Retrievable Endovascular Stent System for Small-Vessel Anatomy: Preliminary In Vivo Data," *Am. J. Neuroradiol.* vol. 26, pp. 862-868 (Apr. 2005).

Liebig, T. et al., "A novel self-expanding fully retrievable intracranial stent (SOLO): experience in nine procedures of stent-assisted aneurysm coil occlusion," *Neuroradiology* vol. 48, pp. 471-478 (Jul. 2006).

Yavuz, K. et al., "Immediate and midterm follow-up results of using an electrodetachable, fully retrievable SOLO stent system in the endovascular coil occlusion of wide-necked cerebral aneurysms," J. Neurosurg. vol. 107, pp. 49-55 (Jul. 2007).

"Penumbra, Inc. Enrolls First Patients in PULSE Clinical Trial to Evaluate a Fully Retrievable, Dense Mesh Temporary Stent for Immediate Flow Restoration in Interventional Acute Ischemic Stroke Treatment," Business Wire, Nov. 1, 2010, downloaded at http://www.businesswire.com/news/home/20101101006991/en/Penumbra-Enrolls-Patients-PULSE-Clinical-Trial-Evaluate.

Wakhloo, et al., "Retrievable Closed Cell Intracranial Stent for Foreign Body and Clot Removal," Neurosurgery, May 2008.

* cited by examiner ated States, behind heart disease and cancer and is the leading cause of severe, longterm disability. Each year roughly 700,000 Americans experience a new or recurrent stroke. Stroke is the number one cause of inpatient Medicare reimbursement for long-term adult care. Total stroke costs now exceeds $45 billion per year in US healthcare dollars.

MONORAIL NEURO-MICROCATHETER FOR DELIVERY OF MEDICAL DEVICES TO TREAT STROKE, PROCESSES AND PRODUCTS THEREBY

RELATED APPLICATION

This application claims the benefit of and priority to U.S. Provisional Application Ser. No. 61/044,392, filed Apr. 11, 2008; U.S. Provisional Application Ser. No. 61/057,613, filed on May 30, 2008; U.S. Provisional Application Ser. No. 61/166,725, filed Apr. 4, 2009; the contents of which are incorporated by reference herein in their entirety.

BACKGROUND OF THE DISCLOSURE

This present disclosure relates to minimally invasive surgical devices, methods and systems. In particular, the present disclosure relates to systems designed to mitigate, extenuate or otherwise address acute stroke.

SUMMARY OF THE DISCLOSURE

Briefly stated, novel devices, improved processes and systems facilitate survival from, and preserve best options for, treatment of stroke.

According to embodiments there is disclosed a process for reperfusion during embolus removal comprising; providing a rapid exchange microcatheter system have at least two lumens, emplacing a microcatheter from the system within a blood vessel in the brain, accessing a desired treatment site, maintaining arterial access including greater support to the arterial tree, and addressing a subject embolus/blood clot.

According to embodiments, a process for making a neuro-monorail microcatheter includes at least one of co-extruding and skiving; co-extruding and skiving and lumen fillings; bonding tubes, and providing a predetermined microcatheter set, cutting a distal segment at 5-50 cm, aligning the same adjacent to a distal section of second microcatheter, placing guidewires in each microcatheter to maintain alignment, and applying short segments of PET along the length to secure and maintain alignment and adjacent status of the resulting device.

According to embodiments, a reperfusion device includes a rapid exchange system comprising a first lumen and a second lumen; a microcatheter disposed within the first lumen, comprising a stroke device, wherein the stroke device is expandable; and a guidewire disposed within the second lumen. The stroke device may comprise radiographic marking elements for visualization during placement, wherein the radiographic marking elements may be disposed at a distal end of the stroke device. The stroke device may be tethered, accessible, and retrievable through the microcatheter.

BRIEF DESCRIPTION OF THE FIGURES

The above-mentioned features and objects of the present disclosure will become more apparent with reference to the following description taken in conjunction with the accompanying drawings wherein like reference numerals denote like elements and in which.

DETAILED DESCRIPTION OF THE INSTANT TEACHINGS

Figure 1:
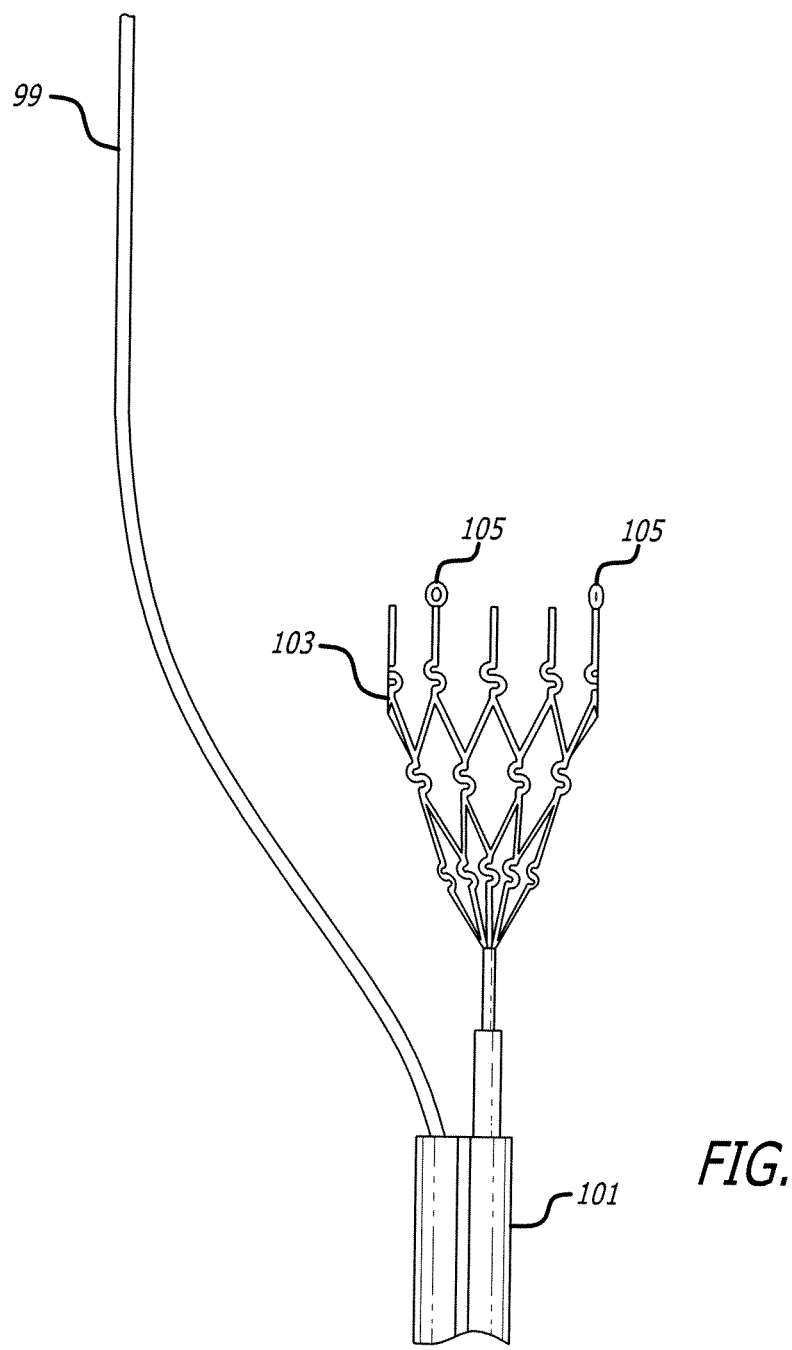
FIG. 1 shows a schematic of an exemplary iteration of a device according to the present disclosure in a first position.

The present inventors have discovered novel ways to treat strokes. This is done by providing microcatheter devices and therapy schemes whereby access is maintained during capture of emboli/thrombi/clot material without compromise to reperfusion of blood flow. The instant disclosures include microcatheters having at least second lumens for vessel stability during removal of emboli and/or in adjunct therapy modes, these devices are referred to as "Rapid Exchange" or RX systems.

The system of the instant disclosure allows and maintains arterial access to treatment sites, and provides enhanced support to the arterial tree, while working as a rapid exchange system. This enables secure capture of emboli/thrombi/clot material by providing support within the vessel. The RX support provided prevents the proximal vessel from buckling or kinking during tensioning upon embolus removal. This is a key feature, in that the literature is demonstrative of ovalizing, whereby stripping of the embolus from capture devices happens when buckling or kinking happens.

Expressly incorporated by reference as if fully set forth herein are U.S. Letters Patents and Publication Nos. 7,018, 372; 6,893,417; and US 2007/0293846; US 2007/0293821; US 2007/0282306; US 2007/0276325; US 2007/0149949; US 2007/0197956.

The pathological course of a blood vessel that is blocked is a gradual progression from reversible ischemia to irreversible infarction (cell death). A stroke is often referred to as a "brain attack" and occurs when a blood vessel in the brain becomes blocked or ruptures. A ischemic stroke occurs when a blood vessel in the brain becomes blocked. Ischemic strokes comprise about 78% of all strokes. A hemorrhagic stroke, which account for the remaining 22% of strokes, occurs when a blood vessel in the brain ruptures. Stroke is the third leading cause of death in the United States, behind heart disease and cancer and is the leading cause of severe, longterm disability. Each year roughly 700,000 Americans experience a new or recurrent stroke. Stroke is the number one cause of inpatient Medicare reimbursement for long-term adult care. Total stroke costs now exceeds $45 billion per year in US healthcare dollars.

Currently there are only two FDA-approved mechanical treatment options for acute ischemic stroke. One option is a thrombo-embolectomy device. In August of 2004, Concentric Medical received FDA approval for its MERCI™ clot removal device. The Merci device is designed to capture an embolus or clot and remove it from the blocked vessel thereby restoring blood flow. The device is designed to be used in conjunction with a microcatheter. The microcatheter must cross the embolus before the Merci device can be deployed. The Merci device design is a cork-screwed guidewire. This device is only able to capture and remove matter that is firm or held together by itself. In most cases Merci breaks up the embolus rather than removes it and is used in combination with drug therapy to restore blood flow. A typical procedure using Merci will take 2-3 hours to restore blood flow if at all and may take multiple passes through the vessel to either capture, macerate or open the vessel. In some cases, the Merci device may capture an embolus but then lose grasp of it and deposit it incidentally in another area arc of the neuro vasculature creating a new stroke in a new territory. In some cases complications such as vessel dissection, perforation and hemorrhage arise as a result of manipulation in the vessel. Some issues in using Merci are that the Merci device itself is a guidewire. Therefore, once it is removed access is lost. Also, as the device is engaging an embolus and being withdrawn proximally, the vessels tend to be pulled with the device and buckle. This action appears to be a great source for the embolus fragmenting and vessel damage. A second option is an aspiration device manufactured by Penumbra, Inc. The embolus is removed by aspirating or sucking from the proximal side. A microwire is passed through the catheter into the embolus to aide in aspirating.

Several methods of treating stroke have been attempted, with varying degrees of success. However, according to the instant teachings, blood can be reperfused or emboli/thrombi/clot material can be removed from the neurovasculature consistently and safely with arterial support and access maintained during the procedure.

Other techniques used in addressing this issue comprise coextruded microcatheters having multi-lumen structures, as would be known to Artisans based on this disclosure and the claims appended hereto.

According embodiments of the present disclosure, an OTW system including a microcatheter having a delivery system tube is combined with a rapid exchange system as discussed above. The OTW system may be configured to fit within a lumen of the RX system. A microcatheter may be configured to fit within another lumen of the RX system. Examples of such a guidewire include Transend® or Synchro® brands. Examples of such a microcatheter include Cordis® MASSTRANSIT® or Renegade™ HI-FLO brands.

In some embodiments, the rapid exchange system comprises an RX microcatheter, a guidewire, a delivery device (e.g., wire or tube), and/or a therapeutic stroke device. In one embodiment, the RX microcatheter is a multi-lumen (e.g., dual-lumen) microcatheter. In one embodiment, the RX microcatheter has a proximal outer diameter of 3.0 F (0.039") and a distal outer diameter of 3.5 F (0.045"). In one embodiment, a first lumen configured to receive a guidewire has a distal inner diameter of 0.017" and the second lumen configured to receive the therapeutic stroke device has a distal inner diameter of 0.023". In one embodiment, the guidewire is a 0.014"×190 cm wire.

The rapid exchange delivery catheter functions with, for example, CORDIS® brands of microcatheters available from them, and may be assembled as detailed below, or as known to those skilled in the art.

Referring now to FIG. 1, according embodiments of the present disclosure, guidewire 99 accesses and crosses a target lesion, providing a pathway for RX microcatheter 101 having at least two lumens. Stroke device 103 is shown in a state of transition from a first (collapsed) position to a second (expanded) position emerging from a lumen of RX microcatheter 101. According to embodiments, guidewire 99 may be at least partially disposed within one of the two lumens of RX microcatheter 101.

Figure 2:
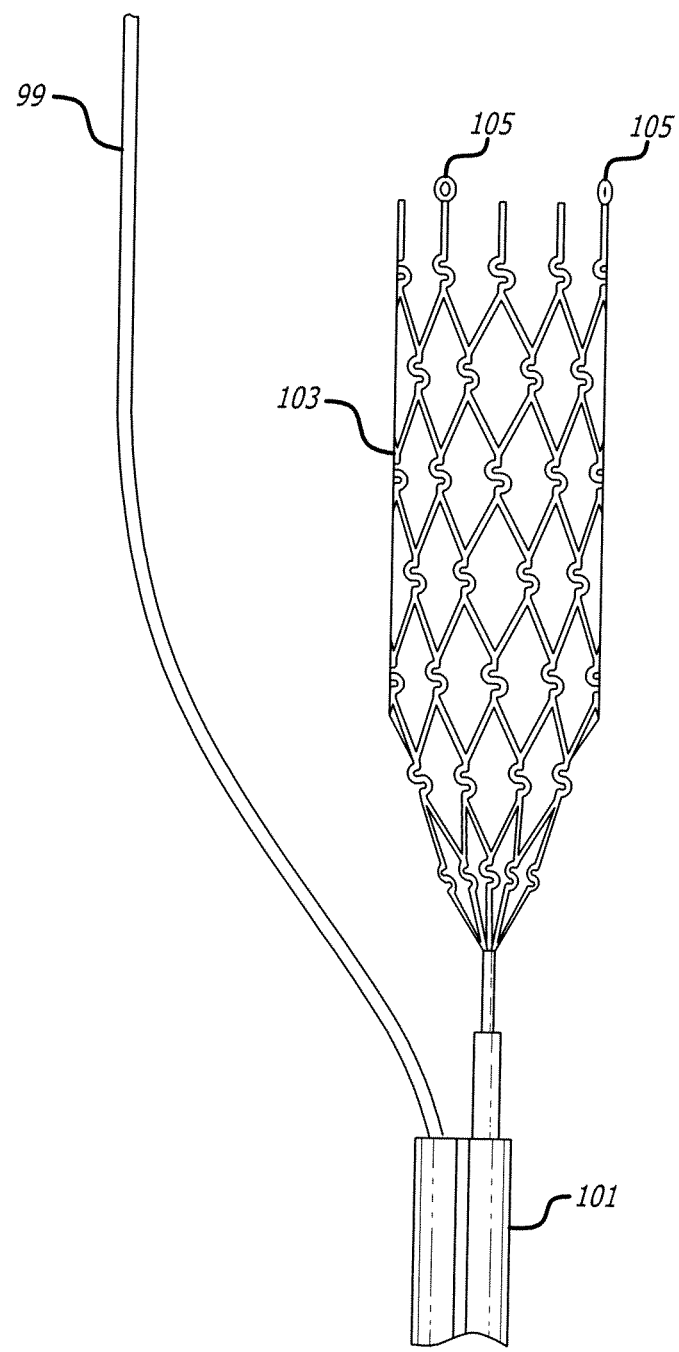
FIG. 2 shows a schematic of an exemplary iteration of a device according to the present disclosure in a second position.

Referring now to FIG. 2, according embodiments of the present disclosure, stroke device 103 includes radiographic marking elements 105 for visualization during placement. Likewise, those skilled in the art readily accomplished using the system of the present invention.

Figure 3:
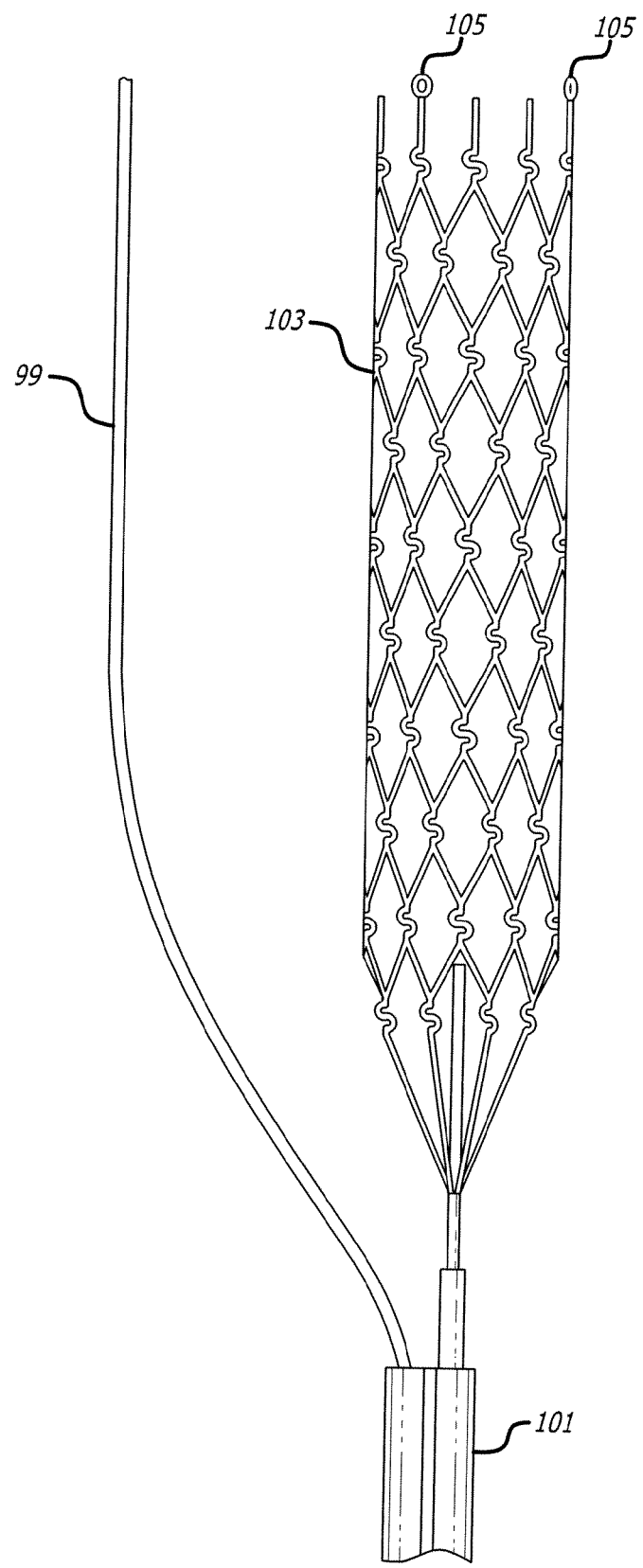
FIG. 3 likewise schematically depicts an exemplary iteration of a device according to the present disclosure in a third position.

Referring now also to FIG. 3, according embodiments of the present disclosure, stroke device 103 is shown in a fully expanded position, whereby it functions consistently and safely such that arterial support is maintained in virtue of guidewire 99 keeping the arterial tree from mechanical stress, while embolus removal, clot capture and other procedures are done. Thus, reperfusion is established and therapy administered without risks to patients present with other devices. According to embodiments, as shown in FIG. 3, stroke device 103 may be tethered such that, while emplaced at a treatment site within a blood vessel, it remains accessible via a microcatheter and readily retrievable therein while maintaining reperfusion of the blood vessel. In one embodiment, the stroke device is tethered to the delivery device via tethered lines. According to embodiments, stroke device 103 may be emplaced on a long-term or permanent basis, or as needed based on the amount and type of recanalization prescribed. According to embodiments, stroke device 103 is self-expandable, such that is may expand substantially radially when removed from within the catheter. According to embodiments, additional therapies may be provided while stroke device 103 is fully expanded, for example, through another lumen of RX microcatheter 101.

According to embodiments of the present disclosure, a process for making a neuro-monorail microcatheter is disclosed. The process may include cutting a first microcatheter at a distal end. A segment may be cut at about 5 cm to 50 cm from a distal end of the microcatheter. The segment of the first catheter may be aligned adjacent to a distal section of a second microcatheter. Guidewires may be placed in each of first and second microcatheters to maintain their respective alignments and keep their lumens open. A resin, such as Polyethylene terephthalate (PET), may be applied in short segments along the lengths of the first and second microcatheters to secure and maintain alignment and adjacent status of the finished device.

According to embodiments of the present disclosure, a first and second catheter, as described above, may be co-extruded and skived, in lieu of the cutting discussed above, and joined as discussed above. In one embodiment, the segment of the neuro-monorail microcatheter configured to receive a guidewire can have a length of about 35 cm to about 40 cm. In one embodiment, the segment of the neuro-monorail microcatheter configured to receive a guidewire can extend 35 cm from the distal end of the neuro-monorail microcatheter.

Figure 4:
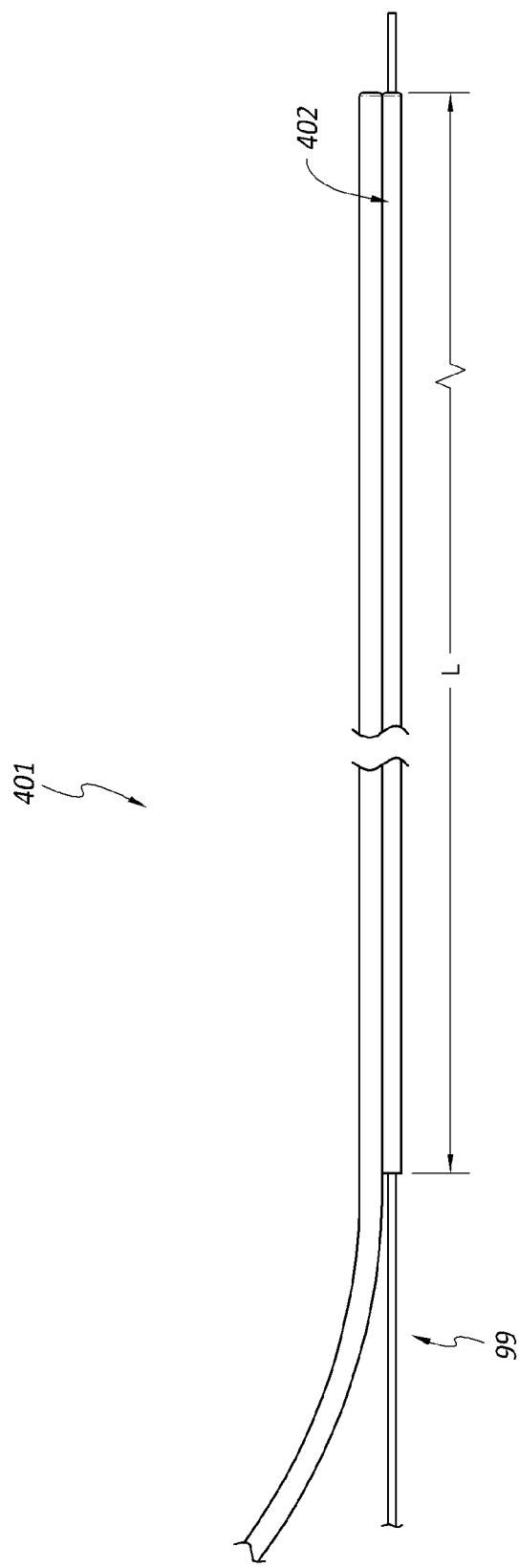
FIG. 4 illustrates a rapid exchange microcatheter in accordance with an embodiment of the invention.

FIG. 4 illustrates a rapid exchange microcatheter 401 in accordance with an embodiment of the invention. The rapid exchange microcatheter 401 includes a first lumen and a second lumen. The second lumen is within a rapid exchange segment 402 of the rapid exchange microcatheter 401 having a length L. As shown, the guidewire 99 can be inserted within the second lumen of the rapid exchange segment 402. The length L of the rapid exchange segment 402 (and the second lumen within) can range from about 5 cm to 50 cm. In some embodiments, the length L can range from about 35 cm to about 40 cm to provide support within the cerebral vasculature (for example, to facilitate movement of the guidewire within tortuous regions of the cerebral vasculature or to prevent buckling or kinking of vessels of the cerebral vasculature).

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A dual lumen reperfusion system for insertion into cerebral vasculature for the treatment of ischemic stroke, comprising, in combination:
    a rapid exchange microcatheter comprising a proximal end, a distal end, a first lumen, and a second lumen separate from the first lumen, both the first lumen and the second lumen terminating distally at the distal end of the rapid exchange microcatheter, the first lumen terminating proximally at the proximal end of the rapid exchange microcatheter;
    wherein the rapid exchange microcatheter is dimensioned for delivery in tortuous cerebral vasculature;
    a delivery device disposed within the first lumen;
    wherein the delivery device is coupled to a stroke device, wherein the stroke device is self-expandable;
    wherein the stroke device is configured to facilitate reperfusion and removal of one or more stroke-inducing emboli within a blood vessel in the brain;
    a guidewire disposed within the second lumen; and
    wherein the second lumen is housed by a segment of the rapid exchange microcatheter that has a length that is less than an entire length of the rapid exchange microcatheter and in the range of about 5 cm to about 50 cm to facilitate movement of the guidewire through the tortuous cerebral vasculature.

2. The reperfusion system of claim 1, wherein the stroke device comprises radiographic marking elements for visualization during placement.

3. The reperfusion system of claim 2, wherein the radiographic marking elements are disposed at a distal end of the stroke device.

4. The reperfusion system of claim 1, wherein the stroke device is tethered to the delivery device and accessible through the microcatheter.

5. The reperfusion system of claim 1, wherein the stroke device is retrievable through the microcatheter.

6. The reperfusion system of claim 1, wherein the second lumen is housed by a segment of the microcatheter that has a length of about 35 cm to about 40 cm.

7. A dual lumen reperfusion system for insertion into cerebral vasculature for the treatment of ischemic stroke, comprising:
    a rapid exchange microcatheter comprising a proximal end, a distal end, a first lumen, and a second lumen separate from the first lumen, the first lumen extending from the distal end to the proximal end, and the second lumen extending from the distal end to a location between the proximal end and the distal end;
    a delivery device disposed within the first lumen, comprising a stroke device, wherein the stroke device is expandable; and a guidewire disposed within the second lumen;

wherein the second lumen is housed by a segment of the rapid exchange microcatheter that has a length in the range of about 35 cm to about 40 cm to provide support within the cerebral vasculature.

8. The reperfusion system of claim 7, wherein the stroke device is coupled to the delivery device via tethered lines.

9. A reperfusion system for insertion into cerebral vasculature for the treatment of ischemic stroke, comprising:

a rapid exchange microcatheter comprising a first catheter and a second catheter, the first catheter having a first length and defining a first lumen extending the first length, the second catheter having a second length and defining a second lumen extending the second length, the first length being greater than the second length, the second catheter extending adjacent to a distal section of the first catheter with a distal end of the second catheter aligned with a distal end of the first catheter;

a delivery device disposed within the first lumen, comprising a stroke device, wherein the stroke device is expandable; and a guidewire disposed within the second lumen.

10. The reperfusion system of claim 9, wherein the first catheter and the second catheter are co-extruded.

* * * * *